United States Patent [19]

Child et al.

[11] Patent Number: 5,012,014

[45] Date of Patent: Apr. 30, 1991

[54] CATALYST PRETREATMENT FOR OLEFIN HYDRATION

[75] Inventors: Jonathan E. Child, Sewell; Byung C. Choi; Francis P. Ragonese, both of Cherry Hill, all of N.J.

[73] Assignee: Mobil Oil Corporation, Fairfax, Va.

[21] Appl. No.: 515,029

[22] Filed: Apr. 26, 1990

[51] Int. Cl.$^5$ .................... C07C 41/05; C07C 29/04
[52] U.S. Cl. .................................. 568/695; 568/897
[58] Field of Search .................. 568/695, 897, 694

[56] References Cited

U.S. PATENT DOCUMENTS 3,678,118  7/1972  Frampton et al. .
4,857,664  8/1989  Huang et al. .................... 568/695

FOREIGN PATENT DOCUMENTS 1173128  12/1969  United Kingdom .

Primary Examiner—Howard T. Mars
Attorney, Agent, or Firm—Alexander J. McKillop; Charles J. Speciale; L. G. Wise

[57] ABSTRACT

A process for production of alcohol or ether by hydration of olefinic feedstock containing at least one lower alkene by contacting the olefinic feedstock and water in a hydration zone with porous solid metal oxide acidic olefin hydration catalyst under olefins hydration conditions. The process is characterized by the step of pretreating porous solid catalyst, such as acid zeolite, prior to contacting with the olefinic feedstock with a wetting agent containing at least one polar aliphatic oxygenated hydrocarbon to substantially wet said solid catalyst and sorb said wetting agent into pores of said solid catalyst. After initiating hydration reaction by feeding the olefinic feedstock and water, increased catalytic activity is obtained. The process is particularly useful for making isopropanol and DIPE from propene and water.

10 Claims, No Drawings

CATALYST PRETREATMENT FOR OLEFIN HYDRATION

This invention relates to olefin hydration, especially for production of di-isopropyl ether (DIPE) from $C_{3}+$ olefinic feedstocks. Particularly, the invention relates to a novel technique for pretreating porous solid metal oxide catalysts to increase catalytic activity.

BACKGROUND OF THE INVENTION

The need to eliminate lead-based octane enhancers in gasoline has provided incentive for development of processes to produce high octane gasolines blended with lower aliphatic alkyl ethers as octane boosters. Supplementary fuels are being vigorously developed in the petroleum refining industry. Lower molecular weight alcohols and ethers such as isopropyl alcohol (IPA), isopropyl t-butyl ether (IPTBE), and diisopropyl ether (DIPE) are in the boiling range of gasoline fuels and are known to have a high blending octane number. They are useful octane enhancers. In addition, by-product propene (propylene) from which IPA and DIPE can be made is usually available in a fuels refinery, typically as a $C_{3}+$ aliphatic stream rich in propene and propane. The petrochemicals industry also produces mixtures of light olefin streams in the $C_2-C_7$ molecular weight range and the conversion of such streams or fractions thereof to alcohols and/or ethers can also provide products useful as solvents and blending stocks for gasoline.

Catalytic hydration of olefins to provide alcohols and ethers is established technology for production of the IPA and DIPE and is of significant commercial importance. Representative olefin hydration processes are disclosed in U.S. Pat. Nos. 4,334,890 (Kochar); 3,912,463 (Kozlowski et al.); 4,042,633 (Woods); 4,499,313 (Okumura et al.); 4,886,918 (Sorensen et al).

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as "Amberlyst 15" may also be used for hydration of light olefins.

Production of ether from secondary alcohols such as isopropanol and light olefins is known. As disclosed in U.S. Pat. No. 4,182,914 (Imaizumi), DIPE is produced from IPA and propylene in a series of operations employing a strongly acidic cation exchange resin as catalyst. Recently, processes for the direct hydration of olefins to provide alcohols and ethers using medium pore shape selective metallosilicate zeolite catalyst, such as zeolite Beta have been disclosed in U.S. Pat. No. 4,857,664 (Huang et al.), incorporated by reference.

Adapting available refinery feedstock to produce these oxygenates simultaneously as octane enhancers can involve two different olefin hydration and etherification processes, i.e. propene hydration-etherification to give DIPE and IPA. Accordingly, a challenge is provided to explore these processes to discover how they may be integrated in a manner more beneficial to the production of high octane gasoline.

It is a main object of this invention to provide a process for production of oxygenated hydrocarbons, such as alcohols and/or ethers in a more economical manner and with improved yields of ethers. It is another object of the present invention to provide an improved reactor start-up procedure to pretreat catalyst for the production of isopropanol and di-isopropyl ether.

SUMMARY OF THE INVENTION

An improved process has been discovered for production of diisopropyl ether, isopropanol or the like by hydration of olefinic feedstock, which comprises contacting the feedstock and water in a hydration zone with porous solid metal oxide acidic olefin hydration catalyst under olefins hydration conditions. The improvement herein comprises pretreating the porous solid catalyst prior to contacting with the solid catalyst with a wetting agent containing at least one polar aliphatic oxygenated hydrocarbon to substantially wet the solid catalyst and sorb the wetting agent into pores of said solid catalyst. In the preferred embodiments, the wetting agent contains isopropanol or isopropanol-water liquid mixture, and the said solid catalyst contains and effective amount of acidic shape selective medium pore zeolite, such as zeolite Beta.

DETAILED DESCRIPTION OF THE INVENTION

The olefins hydration and etherification process of the present invention employs the reaction of propylene with water catalyzed by strong acid to form isopropanol. Reaction may be allowed to continue in the hydration zone to form di-isopropyl ether. The operating conditions of the olefin hydration step include a temperature of about 50° to 450° C., preferably from about 130° to about 220° C. and most preferably from about 160° to about 200° C. The pressure is about 700 to 24000 kPa (100 to about 3500 psi, preferably about 500-2000 psi) a water to olefin mole ratio of about 0.1 to 30, preferably 0.3-5. Olefin hydration to provide ethers and alcohols to produce DIPE and byproduct isopropyl alcohol (IPA) is described in U.S. Pat. Nos. 4,214,107; 4,499,313 and pending U.S. application Ser. No. 336,582 filed Apr. 10, 1989 by Bell et al. The preferred catalytic methods for making DIPE employ solid acid catalysts, such as zeolites Y, Beta and/or ZSM-35 aluminosilicate. DIPE etherification conditions may vary widely in choice of temperature, pressure and reaction time. The preferred method of Bell et al reacts propene with water in a fixed bed of zeolite Beta at about 90° to 200° C. and pressure of at least 4000 kPa. However, it is understood that the unit operations described herein can be conducted with any number of specific process steps within the skill of the art.

The olefin hydration process of this invention can be carried out under liquid phase, vapor phase, supercritical dense phase, or mixtures of these phases in semi-batch or continuous manner using a stirred tank reactor or fixed bed flow reactor. Reaction times of from about 20 minutes to about 20 hours when operating in batch and a LHSV of from about 0.1 to about 10 when operating continuously are suitable. It may be feasible to recover any unreacted olefin and recycle it to the reactor.

The preferred etherification catalyst for the present invention comprises acidic shape selective porous zeolite having a pore size of about 7-8 Angstroms, such as aluminosilicate zeolite Beta. Various solid acid catalysts for hydration of olefins to their corresponding alcohols and ethers have been previously disclosed, such as polysulfonic acid resins, zeolites, etc. Prior pretreating of resin-type catalysts involved wetting with water until breakthrough of the water through the catalyst bed.

It has been found that pretreating zeolite catalyst with an oxygenate wetting agent such as alcohol or an alcohol-water mixture, results in a catalyst with high activity for olefin hydration. The preferred alcohol is the dominant alcohol produced from the hydration reaction of the olefin. For example, isopropyl alcohol when the olefin is propene, 2-butanol when the olefin is a butene, etc.

Pretreatment is effected in a fixed bed downflow reaction at conditions necessary to keep the pretreatment material in the liquid phase with a flow rate adjusted to control the temperature rise due to the heat of adsorption. The catalyst wetting treatment is usually conducted during reactor startup at temperature ranging from ambient to process reaction temperature—e.g., about 20° to 200° C.

The pretreatment is continued until the catalyst is completely wetted, while the catalyst is heated up to reaction conditions. Near the temperature where significant hydration reactions are expected, the pretreating fluid is replaced by the normal feed containing olefin, water and optional recycle streams where appropriate.

Table 1 shows a comparison of two catalysts for the hydration of propylene to isopropanol (IPA) and di-isopropyl ether (DIPE) at identical conditions. The two catalysts, consisting essentially of zeolite Beta, were prepared identically, except that one was pretreated with water at ambient conditions while the other was pretreated with an isopropanol-water mixture at ambient conditions. The catalyst receiving the isopropanol-water mixture in the pretreatment step shows substantially higher conversion of propylene to propanol and water.

|  | H2O Pretreatment | IPA/H2O Pretreatment |
| --- | --- | --- |
| Conditions |  |  |
| Temperature, °C./(°F.) | 165(330) | 165(330) |
| Pressure, psig | 1000 | 1000 |
| C$_3$ = WhSV, Hr$^{-1}$ | 0.5 | 0.5 |
| IPA WSHV, Hr$^{-1}$ | 0.32 | 0.32 |
| H$_2$O WHSV, Hr$^{-1}$ | 0.16 | 0.16 |
| Yields |  |  |
| C$_3$ =, wt % | 44 | 32 |
| IPA, wt % | 20 | 28 |
| H$_2$O WHSV, Hr$^{-1}$ | 9 | 8 |
| DIPE, wt % | 25 | 30 |
| Oligomers, wt % | 2 | 2 |

A theoretical explanation for the observed increase in yields results from the isopropanol saturating the catalyst pores. This prevents the formation of any separate water or olefin phases in the pores during startup. These phases can cause permanent catalyst deactivation. The water phase attacks the crystalline structure of the catalyst, while a highly olefinic phase would deactivate the catalyst via rapid coke formation. The isopropanol also allows controlled quantities of water and propylene to be present homogeneously in the catalyst pores, which allows the reactions to initiate properly when the catalyst is heated to reaction temperatures.

For the treatment to be effective, the added liquid must dissolve high concentrations of water and olefin. The best materials appear to be alcohols and glycols. Secondary or tertiary alcohols with the same carbon number as the olefin feed are most preferred, since they will be formed by the hydration reactions, and therefore will not form any undesired byproducts. C$_2$-C$_6$ aldehydes, esters, ketones and mixtures are also good candidates for the pretreatment, although ethers may not have as beneficial an effect due to their limited solubility in water.

This treatment may be employed with any porous zeolite, or amorphous silica-alumina material, or refractory metal oxide such as silica, alumina, titania and/zirconia, being used in a water/hydrocarbon environment where there is the possibility of forming separate hydrocarbon and aqueous phases. The treatment is useful for processes where water is present in concentrations sufficient to form an aqueous phase.

For the treatment to be fully effective, the catalyst pores should be completely filled with the polar liquid wetting agent. Therefore, the minimum amount of liquid required is approximately equal to the catalyst pore volume.

While the invention has been described by specific examples and embodiments, there is no intent to limit the inventive concept except as set forth in the following claims.

We claim:

1. In the process for the production of diisopropyl ether or isopropanol by hydration of feedstock containing propene, which comprises contacting the propene feedstock and water in a hydration zone with porous solid metal oxide acidic olefin hydration catalyst under olefins hydration conditions, the improvement which comprises:
   pretreating the porous solid catalyst prior to contacting with the propene feedstock with a wetting agent containing at least one polar aliphatic oxygenated hydrocarbon to substantially wet said solid catalyst and sorb said wetting agent into pores of said solid catalyst.

2. The process of claim 1 wherein said wetting agent contains isopropanol or isopropanol-water mixture.

3. The process of claim 1 wherein said solid catalyst comprises acidic shape selective medium pore zeolite.

4. The process of claim 3 wherein said solid catalyst consists essentially of zeolite Beta.

5. The process of claim 4 wherein the wetting agent consists essentially of isopropanol.

6. The process of claim 1 wherein the hydration zone conditions comprise temperature of about 50° to 200° C.

7. A process for the production of alcohol or ether by hydration of olefinic feedstock containing at least one lower alkene by contacting the olefinic feedstock and water in a hydration zone with porous solid metal oxide acidic olefin hydration catalyst under olefins hydration conditions, which comprises:
   pretreating a porous solid catalyst prior to contacting with the olefinic feedstock with a wetting agent containing at least one polar aliphatic oxygenated hydrocarbon to substantially wet said solid catalyst and sorb said wetting agent into pores of said solid catalyst; and
   initiating hydration reaction by feeding the olefinic feedstock and water, thereby obtaining increased catalytic activity.

8. The process of claim 7 wherein the wetting agent contains at least one C$_2$-C$_6$ aliphatic alkanol, ether, aldehyde, ester, ketone, or mixtures thereof with one another or mixtures thereof with water.

9. The process of claim 7 wherein the olefinic feedstock comprises propylene and the wetting agent comprises isopropanol.

10. The process of claim 7 wherein the wetting agent is a hydration product of feedstock olefin.

* * * * *